United States Patent
Schneider et al.

(10) Patent No.: US 9,316,523 B2
(45) Date of Patent: Apr. 19, 2016

(54) SENSOR SYSTEM FOR DETECTING THE FILL LEVEL OF A FLUID IN A VESSEL

(75) Inventors: Jochen Schneider, Wipfeld (DE); Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 720 days.

(21) Appl. No.: 13/576,762

(22) PCT Filed: Feb. 4, 2011

(86) PCT No.: PCT/EP2011/051623
§ 371 (c)(1),
(2), (4) Date: Oct. 16, 2012

(87) PCT Pub. No.: WO2011/095573
PCT Pub. Date: Aug. 11, 2011

(65) Prior Publication Data
US 2013/0026084 A1    Jan. 31, 2013

(30) Foreign Application Priority Data
Feb. 4, 2010    (DE) .......................... 10 2010 001 605

(51) Int. Cl.
*G01F 23/26*    (2006.01)
(52) U.S. Cl.
CPC ............ *G01F 23/266* (2013.01); *G01F 23/268* (2013.01)
(58) Field of Classification Search
None
See application file for complete search history.

(56) References Cited

U.S. PATENT DOCUMENTS

| 4,749,988 | A  | 6/1988 | Berman et al. |
| 5,043,707 | A  | 8/1991 | Heinze |
| 7,509,856 | B1 | 3/2009 | Winkens et al. |
| 2009/0158841 | A1 | 6/2009 | Winkens |

FOREIGN PATENT DOCUMENTS

| CN | 101358868 | | 2/2009 |
| DE | 19651355 | | 6/1998 |
| DE | 199 49 985 | | 5/2001 |
| DE | 10 2004 040441 | | 6/2006 |
| DE | 10 2005 057558 | | 6/2007 |
| EP | 1881307 | | 1/2008 |
| EP | 1881307 | A2 * | 1/2008 |
| GB | 1 472 025 | | 4/1977 |
| JP | H02-168122 | | 6/1990 |
| JP | 2004-279232 | | 10/2004 |
| JP | 2008 000552 | | 1/2008 |
| WO | WO 00/42395 | | 7/2000 |

OTHER PUBLICATIONS

English Translation of EP 1881307 A2 Jan. 2008.*

* cited by examiner

*Primary Examiner* — Terry Cecil
(74) *Attorney, Agent, or Firm* — Jacobson Holman, PLLC

(57) ABSTRACT

The invention relates to a sensor system 10 for the capacitive measurement of the fill level of a fluid medium 22 in a container, preferably a bubble catcher of a dialysis device, comprising a receptacle 30 on which two contact areas are provided for contact with an external surface of the accommodated container and with at least one level detection electrode $C_1$, $C_2$, $C_{11}$, $C_{12}$, $C_{21}$, $C_{22}$ disposed in each contact area for capacitive detection of the fluid level in the container. The sensor system has a coupling measurement device $C_{11}$, $C_{12}$, $C_{21}$, $C_{22}$ for capacitive determination of the correct coupling.

19 Claims, 3 Drawing Sheets

SENSOR SYSTEM FOR DETECTING THE FILL LEVEL OF A FLUID IN A VESSEL

This is a national stage of PCT/EP11/051623 filed Feb. 4, 2011 and published in German, which has a priority of German no 10 2010 001 605.5 filed Feb. 4, 2010, hereby incorporated by reference.

BACKGROUND OF THE INVENTION

The invention relates to a sensor system for the capacitive measurement of the fill level of a fluid medium and a medical device that includes such sensor system.

Sensors are required in a variety of applications in order to measure the fill level of fluids, especially electrically conductive fluids. When the requirements for the purity of the fluid and the prevention of contamination are high, and the fluid must not come into contact with the measurement apparatus, non-invasive measurement systems are suitable, which, for example, detect the fill level using an electrical field and the influencing of this field by the medium to be measured.

A capacitive fill level sensor is known from DE19949985A1, in which a first measurement electrode is attached to a side wall of a container and supplied via an amplifier with a voltage of a particular frequency, so that the electric field lines form in the manner of a capacitor to a second electrode that is disposed below the container. The measurement result may be distorted if, for instance, there is an increase in the container capacitance C (e.g. as a result of the temperature-dependence of the relative dielectric constant $\in_R$). For this reason a compensation electrode C is disposed on the wall of the container such that the field lines from this electrode run essentially through the container walls alone and thereby detect their influence.

As well as this influencing of the detected fill level by, for example, the changing properties of the container wall, the main challenge for the measuring apparatus is posed by the conductivity of the medium to be measured in combination with the susceptibility to wetting of the surface of the container, and the associated film formation on the interior side of the container when the fluid level falls. Possible surge-like variations in the fluid level must also be taken into account. Coupling also poses a problem. Coupling is the indicator of the quality of the accommodation of the container in the measurement apparatus. At the transitional point from the container to the receptacle, coupling capacitances $C_K$ arise. The impedance $Z_C$ of this transition is essentially expressed by the capacitive reactance $X_C = 1/\omega C = 1/2\pi f C_K$.

The measurement path between the capacitor plates of the measurement apparatus is seen as a series connection of parallel-plate capacitors, with the capacitance of a parallel-plate capacitor calculated as: $C = \in_0 * \in_r * A/d$.

$\in_0$ is the dielectric constant (vacuum permittivity), A is the effective area, and d is the separation between the plates, which corresponds to the path of the electric field lines. $\in_R$ is the relative dielectric constant, or relative permittivity, of the medium. In a relevant measurement medium, such as blood, isotonic saline solutions or similar, the relative dielectric constant $\in_R$ is strongly frequency-dependent. On the other hand, the specific conductivity $\kappa$ of the relevant media, at $\kappa = 6$ (blood) or $\kappa = 16$ (NaCl) mS/cm, is dependent on frequency only to a limited extent.

In the measurement apparatus, which will be described later in detail, the coupling capacitances vary in the pF region. The ohmic resistance of the medium is in the single-figure kΩ region. From these values it is clear that in the case of capacitive sensors the measurement result with an operating frequency f in the kHz region up to the single-figure MHz region is mainly determined by the coupling capacitances, since the impedance and phasing of the design is dominated by its reactance.

Known measurement apparatuses are unable to discriminate reliably between a true fill level and merely a thin film or surge of fluid, since the influence, which is only slight, of the difference in ohmic resistance of a massive medium from that of a thin film of fluid is outweighed by the smallest change in the coupling.

The necessity thus results of a high operating frequency, such as for example greater than 75 MHz, as explained in DE 19651355A1 or DE 10 2005 057 558. On the other hand, high operating frequencies, i.e. for example 80 MHz or frequencies in the three-figure MHz region, place high demands on the design of the equipment and circuitry, and in particular the EMC compliance of the design.

SUMMARY OF THE INVENTION

The object of the present invention is non-invasive detection of fill level, in terms of "Level" or "NoLevel", i.e. binary information about whether a sufficient fill level of an aqueous medium such as for example blood, saline solution, dialysate or similar is present or not in a non-conductive container. The aim to be achieved is thereby:

The sensor system must be able to recognize the formation of a film on the inner wall of the container, and/or be able to discriminate between this and the true fill level also in the event of a decrease in the level.

The sensor system must be robust against the possible formation of surges in the area of the sensor elements.

The sensor system must be able to discriminate as far as possible between blood and a thick foam, such as a blood-air mixture. Such a blood-air mixture can form in a venous bubble catcher when air enters the extracorporeal circuit, and collects particularly on the surface of the medium which is to be measured.

The sensor system must be as robust as possible against contact, and the detection of the level should function reliably for both an earthed medium and for a medium which is not connected to a (functional) earth.

The sensor system must be capable of recognizing a possible incorrect accommodation of the container in the receptacle of the sensor system, and in particular able to monitor continuously the correct accommodation.

The sensor system must be robust against contamination such as for instance accumulations of moisture in the measurement area, as in the case of a leakage, and be able to recognize these. In the container according to the invention which will be described in more detail later, the measurement area includes the area outside the container and a receptacle which contains the sensors.

According to the invention a sensor system is provided for capacitive measurement of the fill level of a fluid medium in a container, preferably a bubble catcher of a dialysis device, the sensor system having a receptacle on which two contact areas are provided for contact with an exterior surface of the accommodated container. At least one level detection electrode is located in each contact area for the capacitive detection of the fluid level in the container. The sensor system has a coupling measurement device for capacitive determination of the correct coupling of the container in the receptacle. The coupling is in particular via a mechanical contact, whereby a coupling is also assumed if a (small) air gap remains.

An advantage of this design is that it is non-invasive. This means that the measurement is carried out without the measurement sensors or probes coming into contact with the fluid. The sensor system is thus a type of adaptor, which can be attached to the container. Insufficient coupling, such as for example insufficient mechanical contact, can be detected by the capacitive coupling measurement. Because the above-mentioned capacitive measurements use common electronics for evaluation, costs are saved. The separate measurement of coupling allows the measurement of fill level to be carried out using higher frequencies, without posing the risk that the measured fill level values are distorted when coupling is insufficient due to the high frequencies.

Level detection electrodes advantageously have divided electrode areas, and the coupling measurement device measures the coupling via a capacitive measurement via the electrode areas of each level detection electrode. By means of the different circuitry, only one divided electrode is used in each contact area, which saves component costs. The design of the system can also be configured such that this pair of electrodes is disposed as precisely and closely as possible in the above-mentioned contact area, so that both measurements can be performed in the same place.

In an alternative embodiment, the coupling measurement device has two coupling electrodes on each contact area, which are different from the level detection electrodes. In particular, the coupling electrodes are axially displaced in the longitudinal direction of the container with respect to the level detection electrodes. A functional separation is achieved by this means, and this enables the above-mentioned different measurements to be carried out simultaneously. There is also no necessity for a focus array (as will be described later) for switching the connection of the electrodes to the analyzer.

In addition, the coupling measurement device is capable of detecting both a coupling that is too low, as for example in the case of a gap between the container and the receptacle, and also a coupling that is too high, as for example in the case of fluids or other foreign substances in the contact areas. By means of the double function of the coupling measurement, there is also simple and cost-effective detection of whether the coupling is too high due to contamination, so that a falsely positive result of the level detection measurement can be avoided or recognized.

In one embodiment, if the measurement of the fluid level in the container detects a sufficient level and at the same time the coupling measurement detects an insufficient coupling, the coupling measurement device is capable of triggering a pre-alarm to notify the user of insufficient coupling. Since if there is a positive result of the level detection measurement when the coupling is insufficient, the result of the level detection can fluctuate in an uncoordinated manner and without detectable external influences while the true level is unchanged, this problem can be avoided by a timely warning of the insufficient coupling. The pre-alarm and/or notification of insufficient coupling also prevents a false interpretation of the otherwise non-specific "NoLevel" message, which in practice often leads to overfilling of the bubble catcher.

In a further embodiment the coupling measurement can be used for bubble catcher detection, to check whether the user has inserted the empty bubble catcher correctly.

In particular, a complex total impedance $Z_{tot}$ is determined via the level detection electrodes, and the level detection is carried out via this. The real part of the impedance is preferably evaluated for this. Since the real part is a measure of the electrical resistance in the measured fluid and the resistance is higher in the case of a film on the inner wall of the container or a surge than the resistance of the corresponding fill level, the measurement can be carried out in this manner simply and definitely, and it is possible to distinguish between a film of fluid and the corresponding fill level. With sensors according to the state of the art, on the other hand, it is essentially the phase of the complex total impedance $Z_{tot}$ that is evaluated, with the level detection, i.e. the Level/NoLevel information, being derived from the oscillation or non-oscillation of the oscillator. This can also be understood as an approximate quantification of the phase information. The evaluation of the real part allows the fill level to be detected more accurately, and the real part can also optionally be used (as will be described later) for the detection of thick foam. Correspondingly, because the evaluation is of the real part, a less high operating frequency can be used.

In a further development of the invention, a complex total impedance $Z_{tot}$ is determined via the level detection electrodes, and variations in the total impedance $Z_{tot}$ over time are determined via a demodulator and used in an evaluation unit together with the total impedance $Z_{tot}$ to determine the level detection, in order by this means to recognize inhomogenities in the medium to be measured, such as for example a void fraction. To express this in other terms, this is the capturing of the complex impedance $Z_{tot}$ (magnitude and phase, or imaginary and real parts) with a higher resolution over time. Because bubbles frequently alter their positions on the surface of the fluid—particularly if the container is a bubble catcher—the electrical characteristics of the medium penetrated by the measuring field change, due to the undissolved portion of air mixed in it, considerably more frequently than could occur as a result of filling or emptying the container. Because it has been recognized that such fluctuating measurement results arise through bubbles, these measurement results can be used for a corresponding evaluation.

As an example, the measurement of the level detection is carried out with a frequency greater than 60 MHz, preferably greater than 70 MHz. The essential object of a higher operating frequency is thereby to reduce the impedance of the coupling capacitance as a proportion of the total impedance, to the extent that the almost frequency-independent differences in ohmic resistance between the medium to be measured and a film that is only thin can be discerned clearly and captured.

In a further embodiment the measurement of the level detection is carried out using a frequency lower than 90 MHz, in particular lower than 78 MHz. Measurement systems whose operating frequency is very high, for example in the region of 100 MHz or above, can thereby distinguish reliably between a film of the medium on the inner surface of the container and the fill level of the medium to be measured. However, these systems must in turn forego the ability to check for correct coupling between the sensor system and the container to be monitored before the container is filled. In this respect, a higher operating frequency tends to hinder the determination of the coupling. Here, separate frequencies each with an optimal operating point are defined, in particular for the level detection measurement and the monitoring of the coupling, and the measurement is performed by a switching of the frequencies.

It is advantageous if means are present for generating electrical fields for the level and coupling measurement, and means are present for capturing the complex impedance of different measurement electrodes ($C_{11}$, $C_{12}$, $C_{21}$, $C_{22}$) according to magnitude, phase, and the changes to these over time. Thus the system can connect a network analyzer with different measurement electrodes of the sensor system depending on a control signal. This measurement system is thereby particularly equipped to measure a complex impedance with a high resolution. In this, a focus array is understood particularly as an electronic logic circuit which routes certain input signals to certain output ports depending on its control input. In this manner, a single electronic evaluation unit can be selectively connected by simple means to different electrodes for the above-mentioned measurements.

The container can be the bubble catcher of a dialysis device. Measurement of fluid levels in a container is required in precisely this application, since a constant particular fill level is necessary for the reliable functioning of the device. This fill level can be a minimum level, such as for example a partial filling, or, in the case of a circuit that is free from air, a bubble catcher that is filled as completely as possible. The container can also be a bubble catcher of a medical infusion or transfusion apparatus.

In a corresponding method for the capacitive measurement of the fill level of a fluid medium in a container, the container is held in a receptacle of the sensor system and a level detection device of the sensor system detects by means of capacitance the level of fluid in the container, and the correct coupling of the container in the receptacle is determined by a capacitive coupling measurement device. In this the coupling measurement device can also utilize the measurement results of the level detection, in order by this means to determine correct coupling with certainty, while correspondingly during level detection the measurement results of the coupling measurement can be utilized in order to increase the accuracy of measurement.

The level detection measurement and the coupling measurement are advantageously chronologically staggered. By this means interference to the electrical fields used in the measurements can be avoided, and furthermore in particular the same electrodes, driven at different frequencies, can be used for the different measurements. In addition, via the changes to the measurement results over time conclusions can be drawn concerning possible bubble formation in the medium that is measured.

A medical device, in particular a dialysis device, has a corresponding sensor system and a fluid circulation of an electrically conductive aqueous medium with a bubble catcher. This sensor system is configured to measure the fluid level in the bubble catcher and, depending on the measurement result, to control a feed pump or valve or throttle in the fluid circulation.

The dialysis device is preferably a hemodialysis device for removing urophanic substances from the blood of a patient suffering from renal insufficiency, with an extracorporeal blood circuit provided with a bubble catcher to which the sensor system according to the invention is attached.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
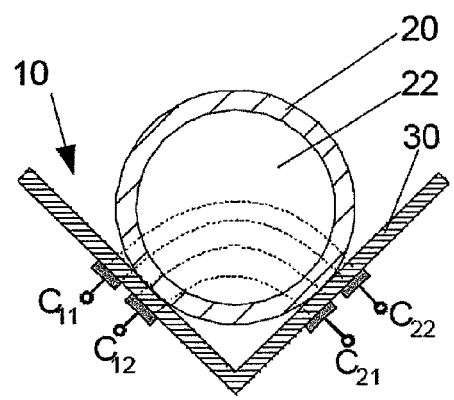
FIG. 1 a cross-section through the measurement apparatus with the field lines of the measurement of the level detection, FIG. 2 an equivalent circuit diagram of the measurement apparatus, FIG. 3 a schematic diagram of the measurement apparatus, FIG. 4 a further cross section through the container with the alternative electrodes and field lines of the level detection, FIG. 5 a cross section through the measurement apparatus with field lines of the coupling measurement, FIG. 6 a cross section through the measurement apparatus with foreign substances in the contact areas between the receptacle and the container, FIG. 7 a timing diagram of the results of the modulator evaluation FIG. 8 a cross section through the container with pressure levers, FIGS. 9A-9D alternative arrangements of the electrodes.

FIG. 1 shows a cross-section through a cylindrical container 20, which in its interior has a fluid area 22. When normally installed the container 20 is orientated vertically, so that the fluid collects in its lower part. The cross section that is shown is thus in the horizontal plane. On two sides of its circumference the container is in line contact with a receptacle 30 of the sensor system 10. "Line contact" means that due to the deformation of the soft material of the bubble catcher a narrow flat-surface contact may also be present. Pressure means 24, which are not shown, ensure that firm mechanical contact is made between the container and the receptacle. In the region of the contact surfaces described above, capacitor plates $C_{11}$, $C_{12}$, $C_{21}$ and $C_{22}$ are disposed. During the measurement of the level detection, plates $C_{11}$ and $C_{12}$ are immediately and directly connected to each other via the control electronics. Electrodes $C_{21}$ and $C_{22}$ are correspondingly connected. When an electrical voltage or frequency is applied to the capacitor plates, the electric field lines that are shown result. The plates are so disposed that as many field lines as possible are guided through the fluid area. There is an angle of 90° between the two flanks of the contact surfaces of the receptacle 30. Angles of between 60° and 150° are advantageous. The contact surfaces can be at any angle to each other. If there is, for example, 180° between the contact surfaces, they are in a single plane, and the bubble catcher is pressed by mechanical means against the contact surfaces. If there is, for example, 360° between the contact surfaces, they are opposite each other, and the bubble catcher is in this case located between the contact surfaces. The fill level can be determined by means of the measurement of the field, as will be described in detail later.

Figure 2:
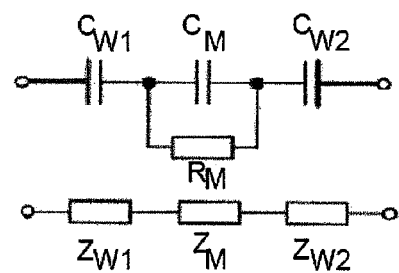

FIG. 2 shows the equivalent circuit diagram for the level detection measurement. In this there are three capacitors, i.e. the capacitance $C_{W1}$ of the first wall of the container, which is penetrated by the field lines, then the capacitance $C_M$ of the medium to be measured, and then the capacitance $C_{W2}$ of the second wall, connected in series. Because the medium that is to be measured is electrically conductive, the resistance $R_M$ of the medium is connected in parallel with $C_M$. The total impedance $Z_{tot}$ is given by: $Z_{tot}=Z_{W1}+Z_M+Z_{W2}$. For the sake of simplicity in the above discussion the capacitance of the wall of the receptacle 30 is considered together with the capacitance of the corresponding wall of the container.

In another alternative embodiment there can be a metalized or metallic surface on the inner side of the receptacle opposite each of the capacitor surfaces $C_{11}$, $C_{12}$, $C_{21}$ and $C_{22}$ which are located on the outer side of the receptacle. These metalized or metallic surfaces are in direct contact with the container 20 and in each case form with the capacitor plates $C_{11}$, $C_{12}$, $C_{21}$ and $C_{22}$ and the measurement medium in the bubble catcher a series connection of two capacitors. The capacitive coupling with the bubble catcher is thereby improved. In this embodiment the electrical contacts are on the side of the capacitor plates $C_{11}$, $C_{12}$, $C_{21}$ and $C_{22}$ which is opposite the container 20.

In an alternative embodiment the capacitor plates $C_{11}$, $C_{12}$, $C_{21}$ and $C_{22}$—in contrast to e.g. FIG. 1—can be disposed not on the side of the receptacle 30 opposite the container, but on the inner side of the receptacle, so that the capacitor plates are directly in contact with the container 20. By this means any influence of the thickness and material of the walls of the receptacle 30 is minimized.

Figure 5:
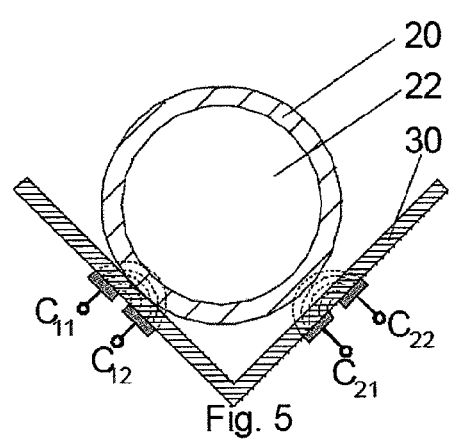

FIG. 5 shows the field lines of an alternative circuit arrangement of the capacitor plates $C_{11}$, $C_{12}$, $C_{21}$ and $C_{22}$, to the effect that the electrical field is established via two neighboring capacitor plates $C_{11}$ and $C_{12}$, or $C_{21}$ and $C_{22}$, in each case. By this means, as will be described later, correct coupling, i.e. contact of the container 20 in the receptacle 30, can be detected. Thus in the embodiments so far described the same electrodes are employed first for the level detection then, in a separate chronologically staggered measurement step, for checking the coupling. The surface of the capacitor surfaces $C_{11}$, $C_{12}$, $C_{21}$ and $C_{22}$ has dimensions in each case of 7×10 mm and the gap between the neighboring capacitor surfaces is 1 to 2 mm. The capacitor surfaces and the gap can also have other shapes and dimensions. This means that the capacitor surfaces in the common circuitry according to FIG. 1 for level detection have dimensions of approximately 15 (or 16) mm×10 mm. In contrast to the state of the art according to DE 199 49 985 A1, measurements are not made with reference to the bottom of the container, but in a section at right angles to the length of the container. In order to be able to determine the level of the fluid correctly, suitable means of fixing (not shown) are used to ensure that the container 20 is held in the receptacle 30 axially aligned in a defined position.

The external diameter of a preferably cylindrical container, such as for example a bubble catcher of a dialysis device, is for example 19-23 mm, with a wall thickness of for example 1.5 mm. The container, preferably composed of plastic, can also have an elliptical or oval basic shape. The container can also be an integral component of a medical blood treatment cassette, in which case the container can take any shape. Thus it is also conceivable that containers have a plurality of flat exterior surfaces, with for example a square outer cross-section. Due to the width of the measurement electrodes and/or the capacitor surfaces, i.e. in the sectional plane shown, sufficient compatibility with containers 20 of varying sizes is ensured.

The complex impedance $Z_{tot}$, which has already been described may be characterized by the magnitude and phase, or by the imaginary and real parts. The actual measurement effect of the level detection is preferably located in the real part of the impedance $Z_{tot}$. The advantageous differentiation and detection of changes in the fill level as against a surge or film results from the differences in the conductance values of the film and the medium, which corresponds to the real part of the impedance $Z_{tot}$. In the case of relatively lower operating frequencies the complex impedance $Z_{tot}$ is dominated by the imaginary part. Thus the differentiation between a surge or film and the fill level can be carried out above all at higher operating frequencies, for example greater than 80 kHz. For EMC reasons, frequencies greater than e.g. 300 MHz are disadvantageous.

Figure 3:
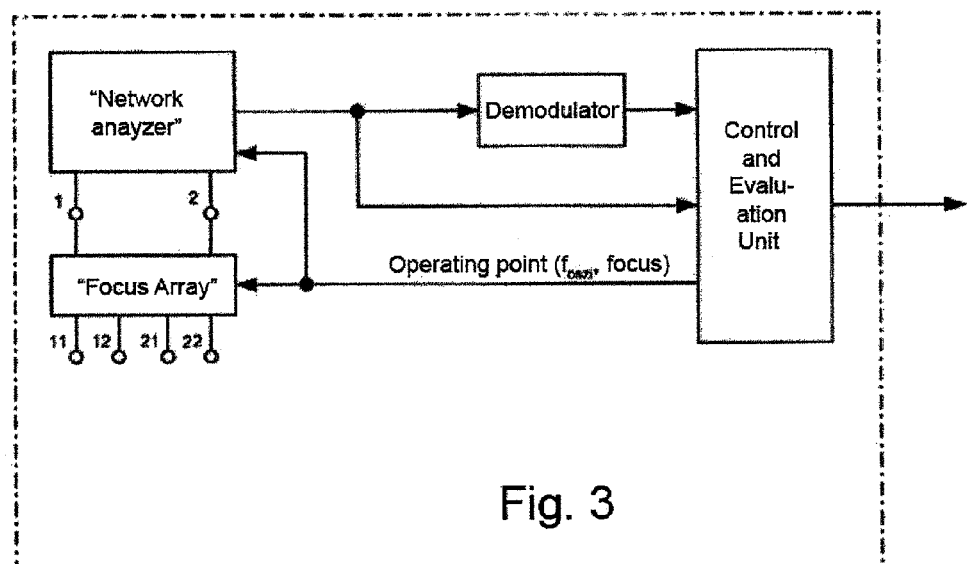

In FIG. 5 there is a certain gap on the right hand side, i.e. at the capacitor surfaces $C_{21}$ and $C_{22}$, between the container 20 and the receptacle 30. This represents insufficient coupling. Thus the electrical field that is shown for detection of the coupling runs mainly through air, and to a lesser extent through the thickness of the walls of the container 20. Insufficient coupling can be detected by an appropriate evaluation of the field profile. Thus, as described above in the context of fill level measurement, the magnitude of the impedance $Z_{11}$ to $Z_{12}$, and/or $Z_{21}$ to $Z_{22}$, can be evaluated. Alternatively, as already known from the state of the art, the phase can be considered. The measurements of the coupling and/or the level detection so far described are chronologically staggered. For this purpose the control and evaluation unit shown in FIG. 3 defines different operating points, and the interconnection of the focus array is correspondingly differentially controlled.

In a first interconnection of the focus array the level detection is carried out. For this purpose the ports 11, 12, 21 and 22, which are connected with the correspondingly designated capacitor surfaces, are interconnected such that 11 and 12 are routed short circuited to contact 1 of the network analyzer and ports 21 and 22, also short circuited, are connected with contact 2 of the network analyzer, so that a field according to FIG. 1 can be generated by the network analyzer. In a second interconnection, port 11 is routed to contact 1 and port 12 to contact 2, so that the coupling (as in FIG. 5 on the left hand side) is carried out. In this case ports 21 and 22 are not connected. In a third interconnection, ports 21 and 22 are connected with contacts 1 and 2 respectively, so that the coupling can be carried out as in FIG. 5 (right hand side). The three measurement results thus obtained from the network analyzer are received by the control and evaluation unit and converted by means of an evaluation logic which will be described in more detail later into the output values which signal to the user the level, the coupling, or the presence of foam. The measurement is carried out if necessary with an operating frequency that is optimized individually for each of the different interconnections of the focus array.

Figure 6:
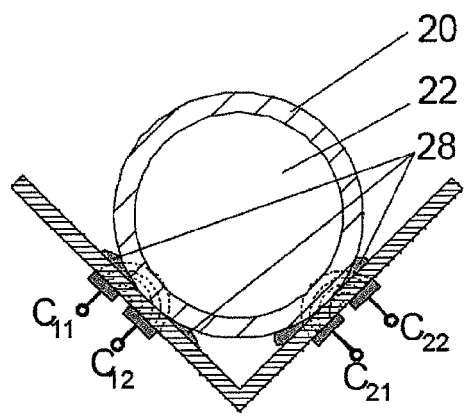

FIG. 6 shows the case in which moisture or a fluid is present in the contact areas between the receptacle and the container. Due to this the measurement results of the coupling measurement are altered such that the coupling is significantly increased. This moisture is also harmful, since it has a detrimental influence on the fill level measurement. The network analyzer detects this increased coupling and notifies the control and evaluation unit, which can issue a corresponding warning to the user.

The following table shows the logical interconnection of the control and evaluation unit. The unit receives the result of the fill level measurement obtained in the first interconnection, which is indicated with 0 (=bad level; =NoLevel) and 1 (=sufficient level). The measurement results of the second and third interconnections are combined with a logical AND operation and passed to the evaluation unit as 0 (=bad coupling) and 1 (=good coupling).

|  | Level measurement | | | | | |
| --- | --- | --- | --- | --- | --- | --- |
|  | 0 | | | 1 | | |
|  | Coupling measurement | | | | | |
|  | 0 | 1 | 2 | 0 | 1 | 2 |
| Evaluation result | alarm | alarm | leakage | pre-alarm | OK | leakage |

The evaluation result is set to "OK" only if the level measurement=1 and the coupling measurement=1, the user being informed of this, for example, by a green light. If the level measurement is 0, a further gradation is carried out depending on the state of the machine: in the operating state of dialysis or rinsing, if the coupling is good (=1) an alarm is given that the level has sunk, and if the coupling is bad (=0) a warning is issued that that the coupling or the position of the bubble catcher may be incorrect. In the operating state of setting up the machine no action is taken, since it is possible that no bubble catcher is installed and thus no level is expected, or no level may even exist. In the operating state after setting up and during filling at least a correctly installed bubble catcher is expected, and if the coupling is good (=1) no alarm is given, but if the coupling is bad (=0) an appropriate warning is issued.

If the level measurement equals 1 and the coupling equals 0, the case of a pre-alarm results. Since the level measurement produces a positive signal, it is not necessary to give an alarm. However, it is possible that at a later time when the level of the fluid itself remains good, the result of the level measurement will change to 0 (=NoLevel) due to the bad coupling, thus signaling a bad level, with this signal in fact being caused by the coupling. By means of the pre-alarm the user is given advance warning of this, with the instruction to improve the coupling. In this way it is possible to avoid false alarms caused by the bad coupling, or above all avoid incorrect interpretations of the measurement results on the part of the user.

It was also stated that the coupling measurement can also detect an increased coupling. This is indicated in the above table with 2, and causes a warning message from a leakage indicator independently of the value of the level measurement.

Figure 7:
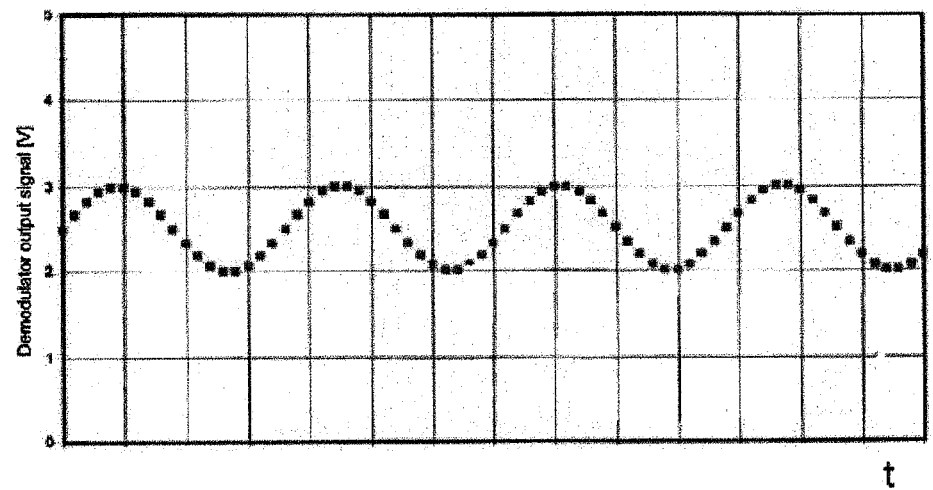

As already mentioned, the sensor system must also recognize a thick foam. Thick foam can form for example when the measured fluid is blood, if leaks occur in the tube system that is connected in a pressure-tight manner to the bubble catcher, as a result of which air can enter the fluid or blood circulation. Due to the behavior of the system as a whole in conveying the fluid, such as in the case of a blood pump, the proportion and the distribution of foam does not remain constant over time. Thus a variation in the measured fields occurs over time, which alters the measured complex impedance $Z_{tot}$. FIG. 7 depicts the waveform of the change of the phase. This waveform is generated by the demodulator from the measured complex impedance $Z_{tot}$ and passed to the control and evaluation unit. When the evaluation unit receives results that fluctuate in this way, the user can be given an appropriate warning (optical, acoustic or haptic) of leakage, or the treatment procedure can be stopped, or not started. The demodulator can also generate the magnitude of the measured complex impedance $Z_{tot}$ and pass this to the control and evaluation unit.

The sensor system is configured such that the individual measurements can be made sufficiently frequently. The measurements are thereby made with a frequency in the millisecond or 1/10 second region.

Figure 8:
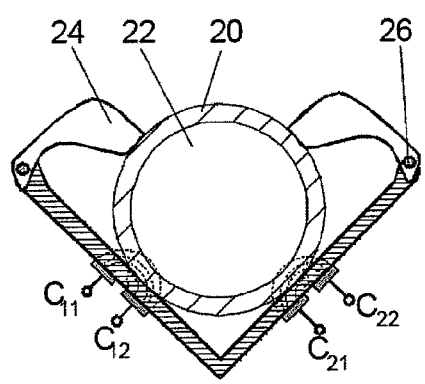

FIG. 8 shows a possible retaining system for the container 20 in the receptacle 30 of the sensor system. In this two arms 24 are mounted in pivots 26 against the receptacle. A spring assistance which is not shown ensures that the container is pressed against the contact surfaces that have already been described.

Figure 4:
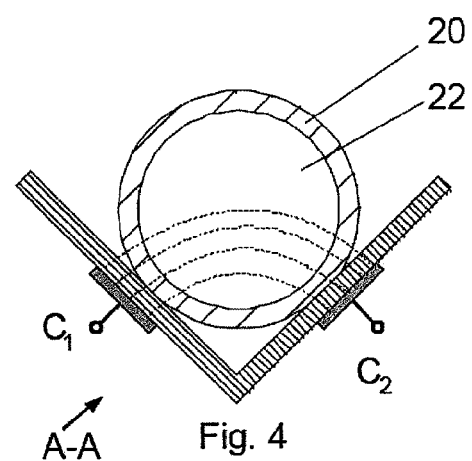
Figures 9A, 9B, 9C, 9D:
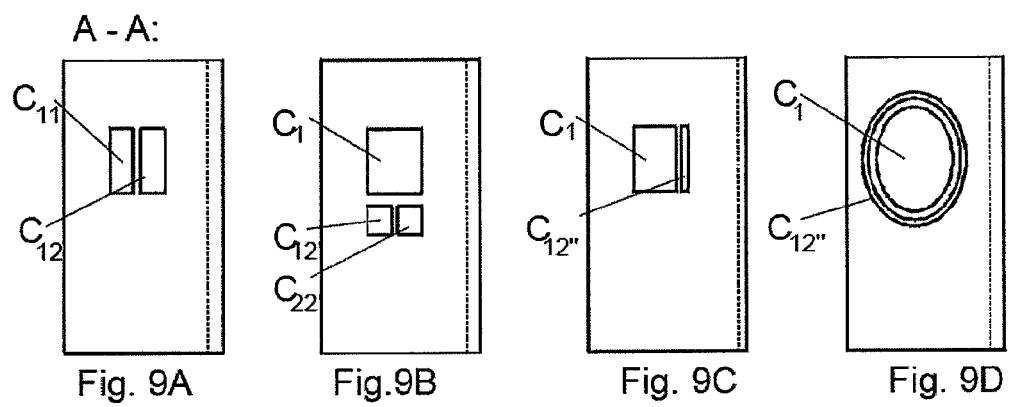

FIG. 9 shows different variants of the electrode arrangement, which correspond to the view A-A in FIG. 4. In FIG. 9A the electrodes $C_{11}$ and $C_{12}$ are the same size, which corresponds to the main embodiment that has been described, in which these uniform electrodes are used in pairs for the level detection.

Alternatively, different electrodes can be used for the level detection and the coupling detection. Thus in FIG. 9B electrode $C_1$ is responsible only for the level measurement, while electrodes $C_{11'}$ and $C_{12'}$ are responsible for the coupling. Because the electrodes are aligned differently in the axial direction of the container, it may be possible to carry out the measurements simultaneously, which naturally requires a different analysis and evaluation unit, not described here in more detail. A single main electrode $C_1$ can also be used for level measurement, as shown in FIGS. 9C and 9D, which operates during the coupling measurement procedures in conjunction with the corresponding auxiliary electrode $C_{12'''}$. While in FIG. 9C the auxiliary electrode $C_{12'''}$ extends along one side of the main electrode $C_1$, in FIG. 9D the main electrode is oval (or alternatively circular), and the auxiliary electrode $C_{12''}$ is located coaxially around its circumference displaced outwards.

The invention can preferably be used in medical devices such as a dialysis device, and in particular the bubble catcher of such a device. The primary purpose of a bubble catcher here is the separation of air by virtue of the widening of its cross-section. Because the outflow from the bubble catcher is on its bottom end face, possible bubbles are separated from the fluid which flows onwards.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. Sensor system (10) for the capacitive measurement of the fill level of a fluid medium (22) in a container, comprising a receptacle (30) on which two contact areas are provided for contact with an external surface of the accommodated container and with at least one level detection electrode ($C_1$, $C_2$, $C_{11}$, $C_{12}$, $C_{21}$, $C_{22}$) disposed in each contact area for capacitive detection of the fluid level in the container, characterized in that the sensor system has a coupling measurement device ($C_{11}$, $C_{12}$, $C_{21}$, $C_{22}$) for capacitive determination of the correct coupling of the container in the receptacle.

2. Sensor system according to claim 1, characterized in that the level detection electrodes comprise divided electrode areas and in that the coupling measurement device determines the coupling via a capacitive measurement via the electrode areas of each level detection electrode.

3. Sensor system according to claim 1, characterized in that the coupling measurement device comprises two coupling electrodes which are different from the level detection electrodes.

4. Sensor system according to claim 3, characterized in that the coupling electrodes are axially displaced in the longitudinal direction of the container with respect to the level detection electrodes.

5. Sensor system according to claim 1, characterized in that the coupling measurement device is capable of detecting both a coupling that is too low, as in the case of a gap between the container and the receptacle, and also a coupling that is too high, in the case of fluids or other foreign substances in the contact areas.

6. Sensor system according to claim 1, characterized in that the coupling measurement device is capable, in the event that the measurement of the fluid level in the container detects a sufficient level and at the same time the coupling measurement detects an insufficient coupling, of triggering a pre-alarm to notify the user of insufficient coupling.

7. Sensor system according to claim 1, characterized in that said sensor system is configured to determine a complex total impedance $Z_{tot}$ via the level detection electrodes, and to carry out the level detection via the evaluation of said total impedance.

8. Sensor system according to claim 7, characterized in that said sensor system is configured to carry out the level detection via the evaluation of the real part of the total impedance.

9. Sensor system according to claim 1, characterized in that said sensor system is configured to determine a complex total impedance $Z_{tot}$ via the level detection electrodes, and to receive variations over time in the complex total impedance $Z_{tot}$ via a demodulator, to be used in an evaluation unit together with the complex total impedance $Z_{tot}$ for determination of the level detection, in order to recognize inhomogenities such as a void fraction.

10. Sensor system according to claim 1, characterized in that said sensor system is configured to carry out the measurement of the level detection with a frequency greater than 60 MHz.

11. Sensor system according to claim 10, wherein said frequency is greater than 70 MHz.

12. Sensor system according to claim 1, characterized in that said sensor system is configured to carry out the measurement of the level detection with a frequency lower than 90 MHz.

13. Sensor system according to claim 12, wherein said frequency is lower than 70 MHz.

14. Sensor system according to claim 1, characterized in that means are present for generating electrical fields for the level and coupling measurement, and means are present for capturing the complex impedance of different measurement electrodes ($C_{11}$, $C_{12}$, $C_{21}$, $C_{22}$) according to magnitude, phase, and the changes to these over time.

15. Sensor system according to claim 1, characterized in that the container is a bubble catcher of a dialysis device, infusion apparatus or transfusion apparatus.

16. Medical device with a sensor system according to claim 1 and a fluid circulation of an electrically conductive aqueous medium with a bubble catcher, wherein said sensor system is configured to measure the fluid level in the bubble catcher and, depending on the measurement result, to control a feed pump or valve or throttle in the fluid circulation.

17. Dialysis device with a sensor system according to claim 1 and a fluid circulation of an electrically conductive aqueous medium with a bubble catcher, wherein said sensor system is configured to measure the fluid level in the bubble catcher and, depending on the measurement result, to control a feed pump or valve or throttle in the fluid circulation.

18. Method for the capacitive measurement of the fill level of a fluid medium in a container, wherein the container is held in a receptacle of a sensor system, the receptacle contacting an external surface of the container at two spaced apart areas, the sensor system including a level detection device comprising a level detection electrode located on the receptacle at each of the two spaced apart areas, each level detection electrode including divided electrode areas, wherein the level of fluid in the container is determined by capacitive measuring between the two level detection electrodes, and the correct coupling of the container in the receptacle is determined by capacitive measuring between the divided electrode areas of each level detection electrode.

19. Method according to claim 18, characterized in that the level detection measurement and the coupling measurement are chronologically staggered.

* * * * *